US006497647B1

(12) United States Patent
Tucker

(10) Patent No.: US 6,497,647 B1
(45) Date of Patent: Dec. 24, 2002

(54) RADIATION AND THERMAL ENERGY SOURCE

(75) Inventor: Robert D. Tucker, North Liberty, IA (US)

(73) Assignee: ATI Medical, Inc., San Diego, CA (US)

( * ) Notice: Subject to any disclaimer, the term of this patent is extended or adjusted under 35 U.S.C. 154(b) by 0 days.

(21) Appl. No.: 09/908,475

(22) Filed: Jul. 18, 2001

(51) Int. Cl.$^7$ ................................................. A61N 5/02
(52) U.S. Cl. ................................................. 600/8; 600/3
(58) Field of Search ......................................... 600/1–8

(56) References Cited

U.S. PATENT DOCUMENTS

| | | |
|---|---|---|
| 4,242,089 A | 12/1980 | Sasaki |
| 4,323,055 A | 4/1982 | Kubiatowicz |
| 4,702,228 A | 10/1987 | Russell, Jr. et al. |
| 4,763,671 A | 8/1988 | Goffinet |
| 4,784,116 A | 11/1988 | Russell, Jr. et al. |
| 4,891,165 A | 1/1990 | Suthanthiran |
| 5,084,002 A | 1/1992 | Liprie |
| 5,133,710 A | 7/1992 | Carter, Jr. et al. |
| 5,405,309 A | 4/1995 | Carden, Jr. |
| 5,429,583 A | 7/1995 | Paulus et al. |
| 5,503,614 A | 4/1996 | Liprie |
| 5,976,067 A | 11/1999 | Tucker et al. |
| 6,074,337 A | 6/2000 | Tucker et al. |
| 6,264,598 B1 * | 7/2001 | Armini ............................ 600/3 |
| 6,273,851 B1 * | 8/2001 | Slater et al. .................... 600/3 |

OTHER PUBLICATIONS

*Practical Aspects of Ferromagnetic Thermoseed Hyperthermia*, Ivan A. Brezovich, Ph.D., et al., *Radiologic Clincs of North America*, vol. 27, No. 3, May 1989, pp. 589–602.

*The effect of catheters and coatings on the performance of palladium–nickel thermoseeds: evaluation and design of implantation techniques*, N. Van Wieringen et al., *Int. J. Hyperthermia*, 1997, vol. 13, No. 2, pp. 187–204.

*The RF Thermoseed–A Thermally Self Regulating Implant for the Production of Brain Lesions*, Charles Burton et al., *IEEE Transactions on Bio–Medical Engineering*, 1971, vol. BME–18, No. 2, pp. 104–109.

*Effect of Thermal Treatment on Heating Characteristics on Ni–Cu Alloy for Hyperthermia: Preliminary Studies*, S.D. Ferguson et al., Jun., 1992.

*Low Curie Temperature Alloys for Interstitial Hyperthermia*, Joe Paulus, Dec. 23, 1991.

*Cytotoxicity of Pd–Co Dental Casting Ferromagnetic Alloys*, Y Kawata et al. *Materials Science*, vol. 60, No. 8, Aug. 1981, pp 1403–1409.

* cited by examiner

Primary Examiner—Steven O. Douglas
(74) Attorney, Agent, or Firm—Knobbe, Martens, Olson & Bear, LLP

(57) ABSTRACT

Implantable seeds, comprising rod-shaped ferromagnetic elements with end caps that contain radioactive pellets, designed for, delivering both thermal radiation and ionizing radiation for treatment of tumorous tissue are described. The implantable seeds can also contain additional radioactive pellets positioned in hollow tubular sleeves that connect a series of ferromagnetic elements. The ferromagnetic material may be a palladium-cobalt (Pd—Co) alloy with a Curie temperature between about 40 C. and 100 C., and the end caps and tubular sleeves may be made of titanium. Alternatively, the ferromagentic elements may comprise rods with longitudinal channels in their outer surfaces, into which radioactive sources are positioned. This assembly is held together by an outer tubular sleeve or coating. The radioactive pellets comprise either palladium-103 or iodine-125. Methods of making the seeds and of delivering treatment to a patient are also described.

62 Claims, 4 Drawing Sheets

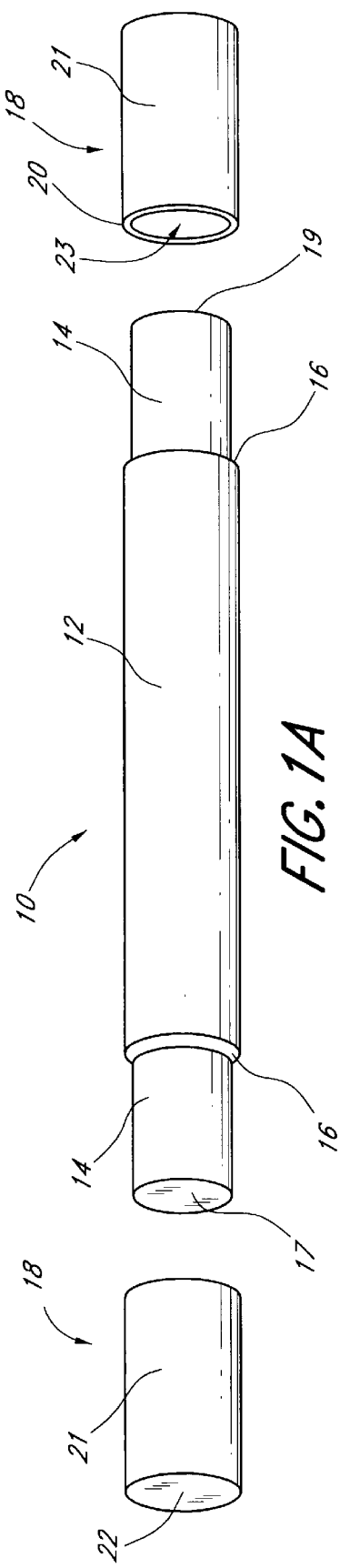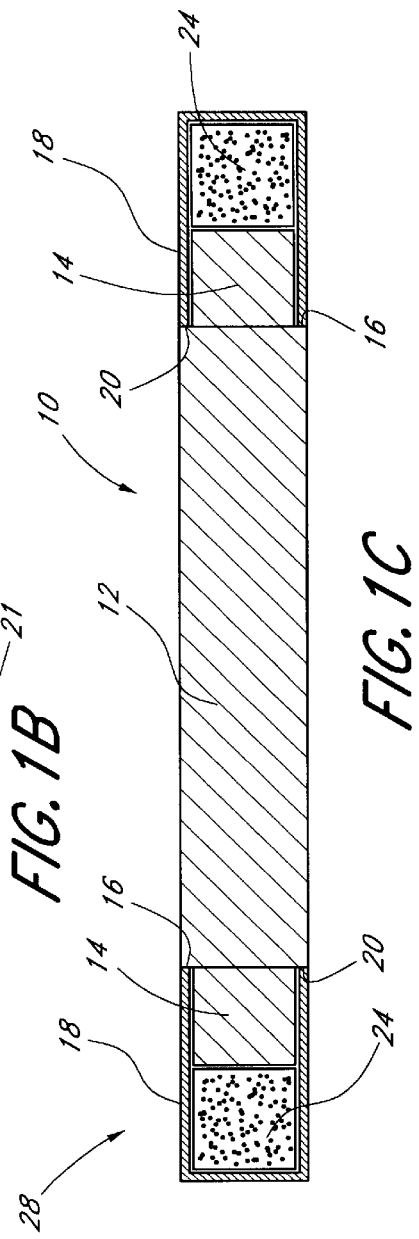

RADIATION AND THERMAL ENERGY SOURCE

BACKGROUND OF THE INVENTION

1. Field of the Invention

This invention relates generally to an apparatus for treating malignant tumors, and, more specifically, to metal seeds that are implanted by injection into tumorous tissue for simultaneous application of thermal energy and radioactive emissions to such tissue.

2. Description of the Related Art

In a journal article entitled "Practical Aspects of Ferromagnetic Thermoseed Hyperthermia," published in the *Radiologic Clinic of North America*, Vol. 27, No. 3, dated May 1989, Ivan A. Brezovich and Ruby F. Meredith, both with the University of Alabama at Birmingham, presented a general treatise on a method of treating tumors by interstitially implanting small pieces of ferromagnetic alloy wire into the tissue and then exposing the subject to an externally applied, oscillating, magnetic field of a predetermined frequency and field strength so as to cause inductive heating of the thermoseeds within the body. This paper points out that by selecting a ferromagnetic material having a suitable Curie point, such a thermoseed becomes self-regulating when the temperature of the seed approaches the Curie point, at which temperature the material becomes non-magnetic. The Carter U.S. Pat. No. 5,133,710 relates to the same technology.

The Paulus et al., U.S. Pat. No. 5,429,583, which is assigned to the assignee of the present application, describes the use of a palladium-cobalt (Pd—Co) alloy as an improved material for such thermoseeds. By properly adjusting the percent by weight of Pd and Co in the alloy, a Curie point temperature (between 40 C. and 100 C.) can be chosen that lies within a range of therapeutic temperatures. Upon exposure to an oscillating magnetic field, the temperature of the thermoseed is self-regulating. The temperature increases until the Curie temperature is reached, at which point, the material becomes non-magnetic, and no additional heating occurs.

It is also known in the art that seeds to be implanted in tumorous tissue can be coated or otherwise treated so as to emit ionizing radiation effective in killing cancerous tissue without excessive damage to surrounding healthy tissue. In this regard, reference is made to Kubiatowicz U.S. Pat. No. 4,323,055, Russell, Jr. et al. U.S. Pat. Nos. 4,702,228 and 4,784,116, Suthanthiran U.S. Pat. No. 4,891,165 and Carden Jr. U.S. Pat. No. 5,405,309, each of which describes techniques for making and utilizing radioactive seed implants and are incorporated by reference herein.

For more than a decade, medical investigators have discussed the synergy of hyperthermia and ionizing radiation in the treatment of several types of tumors. The synergism is believed to be due to some form of combined damage on a cellular level, but increasingly, investigators are theorizing that the increase in blood flow during hyperthermia facilitates the radiation dose by lowering the percentage of hypoxic cells in the tumor. It has been widely known that poorly oxygenated tumors are much more resistant to ionizing radiation than normally oxygenated cell populations. Before the patents cited above, no one appears to have disclosed a combination implant that could produce both thermal and ionizing radiations simultaneously. An implant capable of delivering truly simultaneous thermal and ionizing radiation was a unique advancement, as most clinical research in this area had used separate therapies spaced as close together as possible. The present invention provides just that type of desired implant.

The combination of ionizing radiation and thermal radiation in the seed implants of the related patents cited above offers the further advantage that even when the ionizing radiation given off by the implants has been virtually expended, the magnetic properties of the implants remain intact, allowing for continued hyperthermia or ablation therapy. In normal brachytherapy seeds, after the ionizing radiation has dissipated, the implants are completely inert and have no therapeutic value whatsoever.

The present invention provides an improved implantable seed device, a method of producing the seed and a method of treating a patient with the seed wherein radioactive pellets with sufficient source strength are positioned under encapsulation at least at the ends of the seed and preferably at intervals along the seed providing several improvements over the prior art, as will be discussed below.

SUMMARY OF THE INVENTION

The present invention provides implantable seeds for treating soft tumorous tissue. The seeds comprise rod-shaped ferromagnetic alloy elements with end caps configured as hollow tubes that are closed on one end and open on the other end and contain radioactive pellets and optional spacers. The implantable seeds can further comprise hollow tubular sleeves that connect a series of ferromagnetic alloy elements and also contain radioactive pellets and optional spacers therein. The ferromagnetic alloy may be palladium-cobalt (Pd—Co) with a Curie temperature between about 40 C. and 100 C., and the end caps and tubular sleeves may be made of titanium. The radioactive pellets may comprise palladium-103 or iodine-125. Preferably each Pd—Co element comprises one piece of solid material.

In another embodiment the rod-shaped ferromagnetic element has at least one axially-extending channel along its outer surface. A radioactive source is configured to fit into the channel, and an outer tubular sleeve is positioned coaxially over the rod-shaped ferromagnetic element, thus holding the radioactive source in place.

Another aspect of the present invention provides a method of making an implantable seed for supplying thermal and ionizing radiation to cancerous tissue, comprising providing at least one rod-shaped ferromagnetic alloy element with radioactive sources held in place adjacent to the ends of the element(s) with cylindrical tubes. An external oscillating magnetic field is supplied to act on the ferromagnetic alloy element(s) to produce heat therein. The ferromagnetic alloy may be palladium-cobalt. Preferably the oscillating magnetic field has a maximum flux density of between 25 gauss and 100 gauss and a frequency between 25 kHz and 200 kHz.

Another aspect of the present invention provides a method of treating a patient comprising positioning a plurality of implantable seeds in cancerous tissue so that the longitudinal axes of the seeds are aligned substantially in parallel. The seeds comprise a ferromagnetic material, such as Pd—Co, whose Curie point temperature is in a therapeutic range, preferably between 40 C. and 100 C. Heat is provided by exposing the implantable seeds to an external oscillating magnetic field aligned generally parallel to the longitudinal axes of the implantable seeds. Ionizing radiation is provided from radioactive sources, such as palladium-103 or iodine-125, positioned in cavities enclosed by end caps attached over the ends of the implantable seeds. Additional ionizing radiation may be provided from radioactive sources positioned in cavities within hollow, tubular sleeves that connect adjacent sections of each implantable seed. The spacing between the radioactive sources may be chosen to provide a uniform or predetermined non-uniform dose profile around each implantable seed. Preferably the implantable seeds are exposed to the oscillating magnetic field in a plurality of sessions over a course of treatment, the length of which will be related to the half-life of the radioactive sources.

Further features and advantages of the present invention will become apparent to those of ordinary skill in the art in view of the detailed description of preferred embodiments below, when considered together with the attached drawings and claims.

BRIEF DESCRIPTION OF THE DRAWINGS

FIG. 1A shows an exploded perspective view of an implantable seed for treating cancerous tissue that has one rod-shaped element and two end caps.

FIG. 1B is a thin cross section of an end cap from FIG. 1A, having a radioactive pellet therein.

FIG. 1C is a cross section view of the implantable seed of FIG. 1A, fully assembled.

DETAILED DESCRIPTION OF THE PREFERRED EMBODIMENT

Figure 1D:
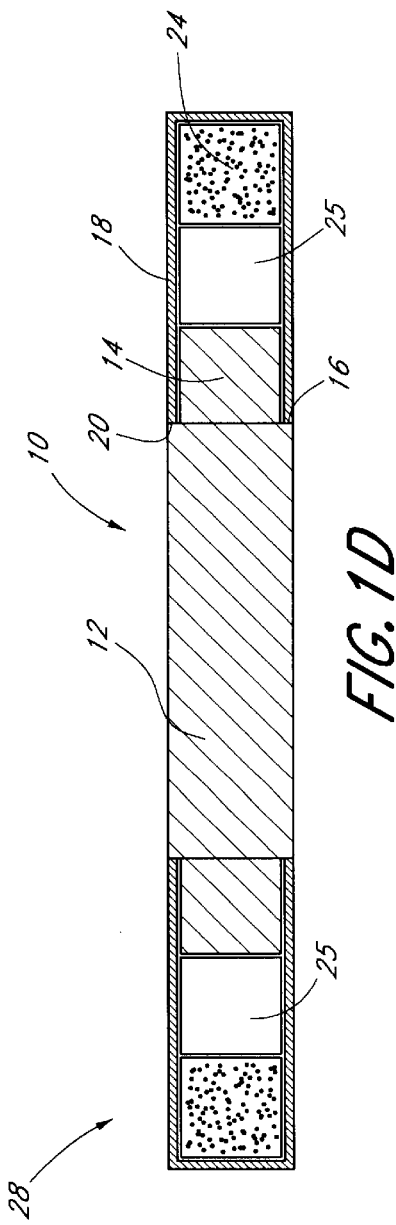
FIG. 1D is a cross section view of the implantable seed of FIG. 1C with both spacers and radioactive pellets in the end caps.

The present invention is related to the subject matter of previously issued U.S. Pat. Nos. 6,074,337, 5,976,067 and 5,429,583, the disclosures of which are incorporated in their entireties herein by reference.

The prior art references set forth in the foregoing "Background of the Invention" teach that it is necessary to encapsulate radioactive material used for radiation treatment to prevent exposure from potentially toxic nuclear decay daughter products. For example, an originally inert coating on an implant might be biocompatible radioactive gold. The nuclear decay daughter product of $Au^{198}$, however, is mercury, hardly a biocompatible and implantable element. Hence, a combination implant, involving Curie point heating and radioactive dosimetry, preferably has an inert and non-radioactive encapsulation or coating to prevent potentially toxic nuclear decay daughter products from being released into surrounding tissue.

Current encapsulation designs, such as reflected in the prior art references cited herein, are not directly convertible into useable thermoseeds for several reasons. First, the space available within the seed is generally too small to contain a sufficiently large amount of low Curie temperature ferromagnetic core material. If the core material is too small, it cannot produce enough heating power when exposed to an oscillating magnetic field to thoroughly elevate the temperature of surrounding tissue. Second, the length of the space within the seed is too short, such that demagnetization end effects predominate and further reduce the efficiency of the thermoseed. To create a combination seed capable of both self-regulated heating and an adequate radiation dose, known prior art devices must be significantly modified.

In the illustrated embodiments that follow, an implantable seed or therapeutic device capable of producing adequate thermal and ionizing radiation doses for treatment of tumorous or other target tissue is discussed. The implantable seed of the illustrated embodiment is cylindrical, but it should be understood that the seed can alternatively have any of a variety of cross sectional configurations such as triangular, square, pentagonal or other polygonal, elliptical, lenticular, or any other shape that is suitable for injection into soft tissue.

In addition, although described as a "seed" in the present description, persons of skill in the art will notice that certain embodiments, particularly those of FIGS. 2A through 2D, disclose devices which can have a significant length. Thus, the term seed is not intended to convey any kind of aspect ratio or maximum length. Rather, the length of the seeds of the present invention is dictated solely by the desired clinical performance and target tissue.

In addition, although the heat and radiation source aspects of the present invention are disclosed in terms of an implantable seed, the structures and features of the present invention can be readily incorporated into other devices. For example, the ferromagnetic material and radioactive source combinations of the present invention can be readily provided on a portion of an elongate probe such as a sharpened rod or needle, having a handle or control on a proximal end. In use, the needle is advanced percutaneously to the treatment site, with the proximal end remaining outside the patient. Following treatment, the needle may be removed from the patient. In addition, the thermal and radiation delivery structures of the present invention can readily be mounted on the distal end of elongate flexible catheter bodies, such as may be percutaneously or otherwise introduced into the femoral artery, brachial artery or other access point and navigated transluminally through the cardiovascular system to a treatment site.

In general, the present invention provides the combination of a radiation source with a material having a Curie point within a therapeutic range. Certain ferromagnetic materials exhibit a suitable Curie point, either alone or as alloyed with other materials, as will be understood in the art. Ferromagnetic materials useful in this role include iron, cobalt, nickel and manganese. Certain ceramic materials also have a Curie point within the appropriate range, but may not generate sufficient heat for therapeutic purposes. Selection of specific materials can be accomplished through routine experimentation by those of skill in the art, taking into account the desired energy output, the desired characteristics of the externally applied, oscillating magnetic field and the size of the device.

It is believed that there are two distinct mechanisms of treatment in two distinct temperature ranges. The range from 42 C. to 46 C. is known as the hyperthermia range wherein tissue is heated above normal temperature and is therefore more susceptible to radiation without necessarily suffering any damage from the heat itself. The range from 46 C. to 100 C. is the ablation range wherein tissue is damaged or destroyed from the heat itself. In general, a lower radiation dose can be used in the ablation range than in the hyperthermia range with good therapeutic results.

Preferably, the ferromagnetic material exhibits a Curie point within the range of from about 40 C. to about 100 C., and, generally within the range from about 40 C. to about 46 C. Certain specific embodiments have a Curie point at about 42.5 C.

In addition, the material also desirably has sufficient power output to elevate local temperatures to the above recited temperature values. Sufficient power output generally means greater than about 100 milliwatts per centimeter of length of the seed or rod. Power outputs in excess of about 150 or 200 milliwatts per centimeter length are often preferred, and power outputs of from about 250 milliwatts per centimeters to about 350 milliwatts per centimeter may also be used.

The radiation source component of the present invention can comprise any of a variety of isotopes for emitting gamma, beta or x rays. The radiation source can be in the form of a solid material for entrapment within the cavities as will be discussed below, or in the form of powders, coatings, ion implantation, or other forms depending upon the desired activity, clinical performance and manufacturing techniques. In view of the foregoing, it should be appreciated by those of skill in the art that the following description is exemplary only, and that many variations of the technology described specifically herein will become apparent to those of skill in the art in view of the disclosure herein.

With reference to FIG. 1A, a rod 10, made of a ferromagnetic material, such as nickel-copper, iron-platinum, nickel-silicon, nickel-palladium or palladium-cobalt, with a Curie point temperature between about 40 C. and 100 C., whose middle section 12 is cylindrical in shape, is shown. For application in the prostate, the diameter of the middle section 12 is generally between about 0.8 mm and about 1.2 mm.

The rod end sections 14 of the rod 10 have a smaller diameter than the middle section 12, and the smaller diameter is preferably between about 0.68 mm and 1.20 mm. The length of each rod end section 14 is preferably between about 0.8 mm and 1.2 mm. There are steps 16, perpendicular to the rod surface, that make the transition from the thicker middle section 12 to the rod end sections 14 of the rod 10. The overall length of the rod 10, from a first end surface 17 to a second end surface 19, including the middle section 12 and both rod end sections 14 is between about 6 mm and 14 mm. Preferably the rod is solid from end to end and can deliver power in excess of 150 mw/cm (milliwatts/centimeter), more preferably between about 250 and 350 mw/cm along its length when subjected to an oscillating magnetic field.

End caps 18 are sized to fit over the rod end sections 14 of the Pd—Co rod. Preferably, the end caps 18 comprise a cylindrical side wall 21, but they may have any other configuration that is suitable for attachment to the Pd—Co rod so that the overall shape of the seed is suitable for injection into soft tissue. The end caps 18 each have one open end 20 and one closed end 22, and at least one cavity 23 therein. The outer diameter of the end caps 18 at the open ends 20 may be the same as the outer diameter of the middle section 12 of the Pd—Co rod 10 at the steps 16, to provide a substantially uniform external profile along the length of the seed.

The depth or length of the cavity 23 in the axial direction is greater than the axial length of the rod end section 14, thereby preserving a cavity 23 in the assembled device. Preferably, the depth of the cavity 23 in the axial direction exceeds the axial length of the rod end section 14 by a sufficient distance to accommodate a radioactive source capable of delivering an absorbed dose of at least about 115 to 160 gray over its useable lifetime. Of course, the absorbed dose desired for a specific treatment situation may be different, and a wide variety of radioactive sources and desired doses can be accommodated in the present invention. The volume of the cavity 23 may be varied, depending upon the nature of the source. In an embodiment having a rod end section 14 within the range of from about 0.8 mm to about 1.8 mm in length, the length of the end cap 18 will preferably be at least about 1 mm and generally from about 2 mm to about 5 mm in the axial direction. The depth of the cavity 23, of course, will be only slightly less than the length of the end cap 18. In one embodiment, in which the length of the rod end section 14 is about 1 mm, and the source is palladium-103, the depth of the cavity 23 in end cap 18 is about 2.5 mm. In general, the length of the rod end section 14 will be approximately equal to the desired overlap length between the rod 10 and the end cap 18 in the assembled device. The optimal overlap can be determined through the exercise of routine skill in the art in view of the manner in which the cap 18 is secured to the rod 10, as will be discussed below.

FIG. 1B shows a thin cross section of the end cap 18, into which a radioactive pellet 24 has been placed. The illustrated radioactive pellet 24 is shaped to conform to the cavity 23 inside of the end cap 18. Preferably, the pellet 24 fits snugly against the closed end 22 of the end cap 18, and leaves little or no space between the outer circumference of the pellet 24 and the inner circumference of the end cap 18. When the pellet 24 is in place in the end cap 18, there is at least enough space remaining at the open end 20 of the end cap 18 for making a sufficient connection to the rod 10 (FIG. 1A).

The radioactive pellet 24 can comprise any of a variety of isotopes, depending upon the desired delivered dose, penetration depth into the tissue, and other clinical performance and product shelf life parameters. In addition, for low energy isotopes, the composition of the cap 18 may limit isotope choice as will be apparent to those of skill in the art. For example, beta emitters (such as phosphorus-32) have relatively low penetration. Certain higher energy sources such as gamma emitters or x-ray emitters have greater tissue penetration but introduce additional complexity during manufacturing and handling. Higher energy sources which may be useful in the context of the present invention include gold-198 ($Au^{198}$), iodine-125 ($I^{125}$) and palladium-103 ($Pd^{103}$). Preferably the radioactive pellet 24 comprises $Pd^{103}$ or $I^{125}$. Blends of the foregoing may also be used.

The source strength of a radioactive source is related to the number of radioactive events or particles emitted per unit time interval. Given two samples of material with identical half-lives, where one has twice the mass of the other, the larger sample will also have a source strength twice as large. The radiation dose delivered to surrounding tissue is proportional to the source strength of the radioactive emitter.

Given two sources of equal material with different half-lives, initially the source with the shorter half-life will have a greater source strength. Eventually its activity level will fall below that of the other source as the amount of radioactive material in the first source will be depleted faster. Suitable radioactive implants should be capable of delivering more than about 115 gray (joules/kg absorbed radiation dose) and in some embodiments at least about 160 gray over their usable lifetimes. Thus, in designing a radioactive implant, both the half-life and the source strength are important considerations. The half-life is determined completely by the type of radioisotope, and the source strength is determined by both the particular isotope and the amount of radioactive material present. The half-life of $Pd^{103}$ is 17 days, and the half-life of $I^{125}$ is 60 days.

The decay particle energy of the radioisotope is completely unrelated to its half-life or source strength. Typically the decay particle originates from a specific atomic or nuclear event which, in turn, causes the release of x rays of characteristic energy. For example, both $Pd^{103}$ and $I^{125}$ isotopes decay by electron capture, wherein an inner shell electron is absorbed by the nucleus. An outer shell electron jumps down to fill the inner shell vacancy, releasing its excess energy by emitting a characteristic x ray. Due to small variations in the electron energies, characteristic x-ray energies typically fall over a small range. For $Pd^{103}$, these x rays have energies from 20 to 23 keV; for $I^{125}$ these x rays have energies from 25 to 32 keV.

The end cap 18 is made preferably of a material that is biocompatible and that efficiently transmits x rays or other selected decay particles. The end cap material and wall thickness are chosen to allow good transmission of ionizing radiation from the radioactive pellet inside the cap to the surrounding tissue. In one embodiment, the end cap 18 is made of titanium (Ti). The thickness of the Ti end wall 22 and side wall 21 in the end cap 18 are preferably between about 0.02 mm and 0.13 mm.

FIG. 1C is a side elevational cross-sectional view through a fully-assembled two-source implantable seed according to one embodiment of the current invention. The inner circumference of the end caps 18 fits snugly over the outer circumference of the rod end sections 14 of a Pd—Co rod 10. The open ends 20 of the end caps 18 fit snugly against the steps 16 of the Pd—Co rod. The outer diameter of the end caps 18 and the outer diameter of the middle section 12 of the Pd—Co rod 10 are substantially the same at this junction, as discussed above for FIG. 1A, making the outer surface of the implantable seed 28 smooth and continuous throughout.

The end cap 18 may be connected to the rod 10 in any of a variety of manners, as will be apparent to those of skill in the art in view of the disclosure herein. In general, the connection between the end cap 18 and rod 10 will take into account the respective materials of these two components, together with the desired integrity of the bond. For example, for metal end caps 18 and rods 10, any of a variety of welding, soldering, brazing or other metal bonding techniques may be used. Interference fit, such as snap fit constructions may also be used. Complementary surface structures such as a male thread on the end section 14 for cooperation with a corresponding female thread on the end cap 18 may also be used. Preferably, the bonding technique will both provide sufficient physical integrity to prevent detachment of the cap 18 during normal use conditions, as well as enable the finished seed to qualify as a sealed radioactive source. In an embodiment having a titanium end cap 18 and a Pd—Co rod 10, the end cap 18 may be welded to the rod 10. In other embodiments, such as toleranced or interference fit structures, additional bonding agents such as adhesives or other polymeric materials may be utilized to assist in meeting the sealed radioactive source standard. If a polymeric species is utilized as a bonding agent or sealing agent, interactions should first be determined between the particular polymeric species and the nature and activity of the isotope, in view of the degradation which can occur to polymeric materials when positioned in a radioactive field.

The radioactive pellet 24 has a length that fits into the space remaining in the end cap 18 after the Pd—Co rod has been attached. Preferably, the pellet 24 fits snugly against both the inner surface of the closed end 22 of the end cap 18 and the end surface 17 of the Pd—Co rod 10. The lengths of the end caps 18 can be adjusted to accommodate radioactive pellets 24 of various lengths.

Alternatively, it may be desirable to position the radioactive source a distance away from the Pd—Co rod in order to decrease attenuation of radiation by the Pd—Co adjacent to the rod. As shown in FIG. 1D, a spacer 25 can be placed between rod end section 14 and radioactive pellet 24 in the end cap 18. Preferably the spacer comprises a material that is a good transmitter of radiation, for example, silica glass, silicon, beryllium or aluminum.

In another embodiment of the current invention, a multi-element implantable seed wherein the ferromagnetic rod comprises at least two separate pieces joined together by tubular sleeves which also hold radioactive pellets that act as point sources, can be understood with reference to FIGS. 2A–2D. This arrangement can accommodate three or four or five or more radioactive point sources arranged spaced apart along the length of the seed. The skilled artisan can choose the number of point sources and the distance between the sources to tailor the ionizing radiation dose distribution provided by the seed for optimal treatment of the surrounding tissue.

Figure 2D:
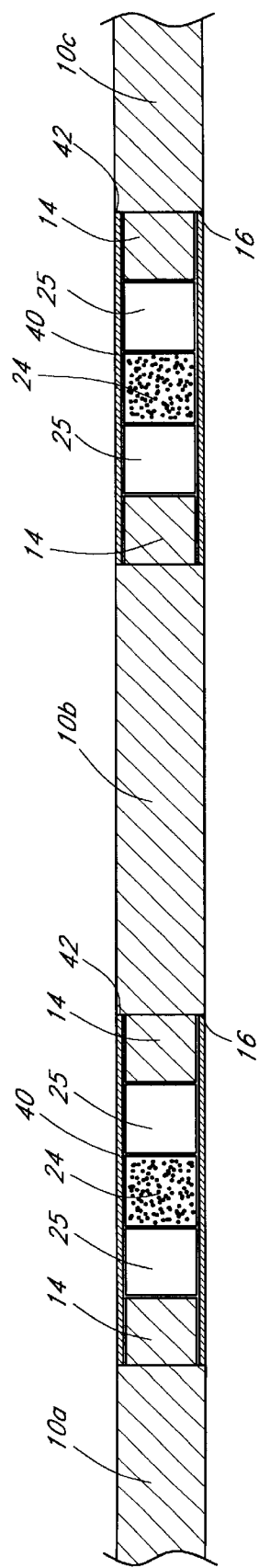
FIG. 2D is a cross section view of a portion of the multi-element implantable seed of FIG. 2C with both spacers and radioactive pellets in the tubular sleeves.
Figure 2A:
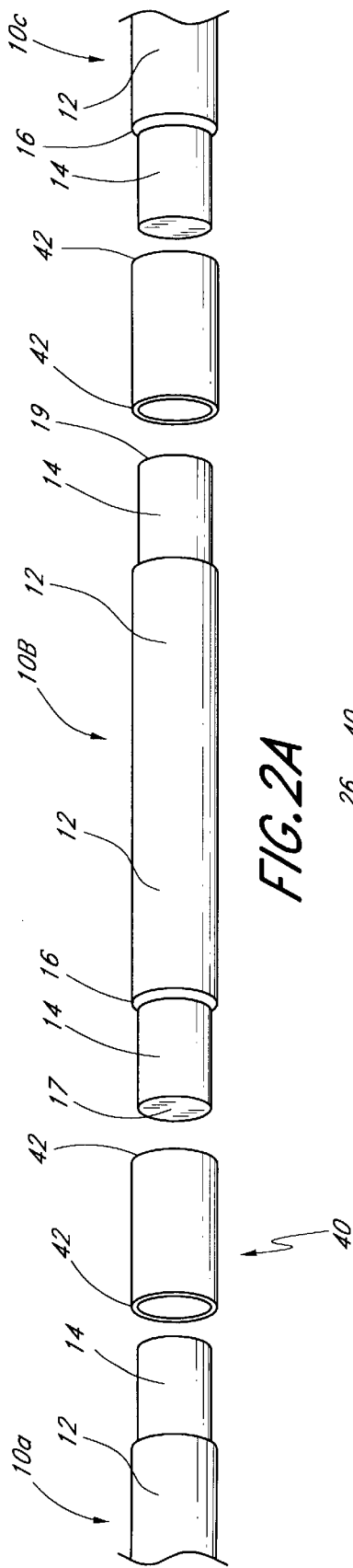
FIG. 2A shows an exploded fragmentary view of a portion of a multi-element implantable seed for treating cancerous tissue wherein adjacent elements are joined together by tubular sleeves.

FIG. 2A is an exploded side elevational view of a portion of a multi-element implantable seed that shows ferromagnetic rods 10a, 10b, 10c preferably comprising Pd—Co with a Curie point temperature between about 40 C. and 100 C., as has been described above with reference to FIG. 1A. In this illustration, the middle section 12 of each rod 10 is cylindrical in shape, preferably with a diameter between about 0.8 mm and 1.2 mm. Many of the details of the embodiment of FIGS. 1A–1D discussed supra may be readily applied to the embodiment of FIGS. 2A–D, which will be discussed only briefly below.

The rod end sections 14 have a smaller diameter than the middle section 12, and the smaller diameter is preferably between about 0.68 mm and 1.20 mm. The length of each rod end section 14 is preferably between about 0.8 mm and 1.2 mm. There are steps 16, which may be perpendicular to the rod surface, that make the transition from the thicker middle section 12 to the thinner rod end sections 14. The overall length of each rod 10a, 10b and 10c, from one end surface 17 to another 19, including the middle section 12 and both rod end sections 14, is between about 6 mm and 14 mm. Preferably the rod is solid from end to end and can deliver power in excess of 150 mw/cm, more preferably, between about 250 and 350 mw/cm, along its length when subjected to an oscillating magnetic field.

The tubular sleeve 40 is a hollow tube with two open sleeve ends 42. The tubular sleeve 40 is at least long enough to accommodate a radioactive pellet 24 and two rod end sections 14 of the adjacent Pd—Co rods 10, one at each sleeve end 42.

Preferably the tubular sleeve 40 is between about 3.0 mm and 6.0 mm in length. The outer diameter of the sleeve ends 42 is substantially the same as the outer diameter of the adjacent portions of the middle section 12 of the Pd—Co rod 10 at the steps 16.

Figure 2B:
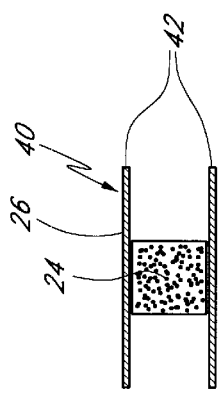
FIG. 2B is a thin cross section of a tubular sleeve from FIG. 2A, having a radioactive pellet therein.

FIG. 2B shows a thin cross section of the tubular sleeve 40, into which a radioactive pellet 24 has been placed. The radioactive pellet 24 is shaped to conform to the central portion of the tubular sleeve 40. Preferably, the pellet 24 fits snugly against the wall 44 of the tubular sleeve 40, with little or no space between the outer circumference of the pellet 24 and the inner circumference of the tubular sleeve 40. When the pellet 24 is in place in the tubular sleeve 40, there is at least enough space remaining at each open end 42 of the tubular sleeve 40 for making connections to a Pd—Co rod 10 (FIG. 2A) at each sleeve end 42. Preferably the radioactive pellet 24 comprises palladium-103 ($Pd^{103}$) or iodine-125 ($I^{125}$).

Figure 2C:
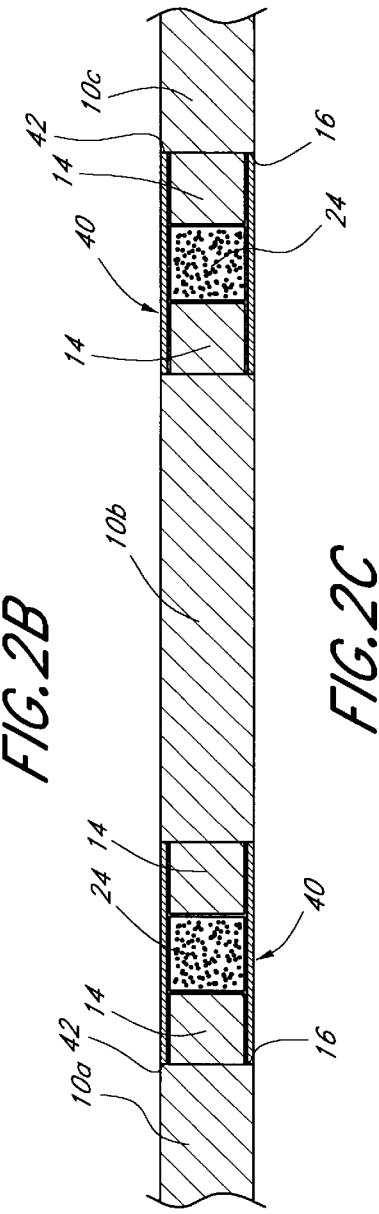
FIG. 2C is a cross section view of a portion of the multi-element implantable seed of FIG. 2A, fully assembled.

The tubular sleeve 40 is made preferably of a material that is biocompatible and that transmits x rays or other radioactive species well. More preferably, the tubular sleeve 40 is made of titanium. The thickness of the Ti wall 26 in the tubular sleeve 40 is preferably between about 0.025 mm and 0.050 mm. FIG. 2C is a longitudinal cross-sectional view through the middle of a fully-assembled, multi-element implantable seed. The inner circumference of the tubular sleeve 40 fits snugly over the outer circumference of the rod end sections 14 of the Pd—Co rod 10. The open ends 42 of the tubular sleeve 40 fit snugly against the steps 16 of the Pd—Co rod. The outer diameter of the tubular sleeve 40 and the outer diameter of the middle section 12 of the Pd—Co rod 10 are the same at this junction, as discussed above for FIG. 2A, making the outer surface of the implantable seed 28 smooth and continuous throughout. The tubular sleeve ends 42 are connected such as by welding to the Pd—Co rod 10 at the junctions.

The radioactive pellet 24 has a length that fits into the space remaining in the tubular sleeve 40 after the Pd—Co rods 10 have been attached at both ends. Preferably the pellet 24 fits snugly against the end surfaces 17 of the Pd—Co rods 10 on each end of the tubular sleeve 40. The length of the tubular sleeve 40 can be adjusted to accommodate radioactive pellets 24 of various lengths and spacers if desired. The outermost ends of the multi-element implantable seed can be sealed off with end caps as shown in FIGS. 1A–1D.

The length of the Pd—Co rods and any spacers used determines the spacing between radioactive pellets, which act as radiation point sources in the implantable seed. The skilled artisan can choose a spacing and a number of radioactive pellets to provide a desired dose distribution to the soft tissue surrounding the implantable seed. It may be desirable to position the radioactive source a distance away from the Pd—Co rods in order to decrease attenuation of radiation by the Pd—Co adjacent to the source. As shown in FIG. 2D, spacers 25 can be placed between rod end sections 14 and radioactive pellet 24 in the tubular sleeve 40. Preferably the spacers comprise a material that is a good transmitter of radiation, for example, silica glass, silicon, beryllium or aluminum.

Metal tubes with their own structural integrity are not the only means for connecting ferromagnetic rods and enclosing radioactive pellets and spacers. For example, tubes can be made of other materials, such as plastic or glass. Alternative arrangements can also be used. Rods, pellets and spacers can also be held together by films or coatings applied by dipping, spraying or wrapping. Preferably films or coatings are at least 10 $\mu$ms in thickness and can be as thick as several $\mu$ms.

Figure 3A:
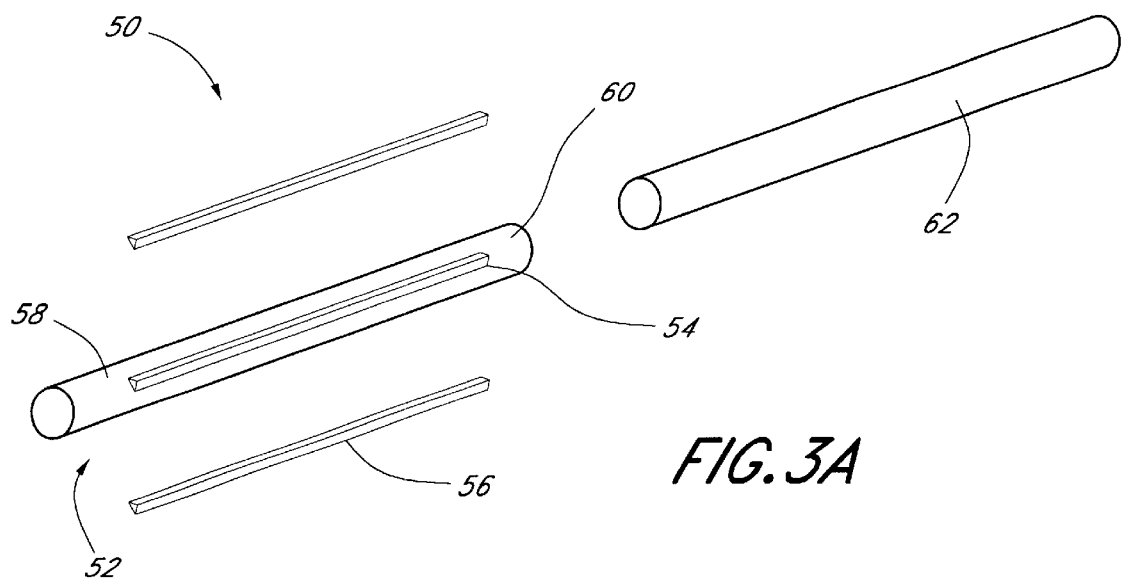
FIG. 3A is an exploded perspective view of an alternate implantable device in accordance with the present invention.
Figure 3B:
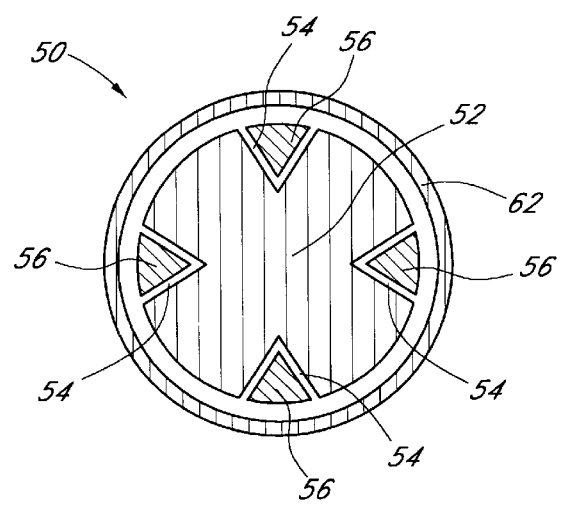
FIG. 3B is a transverse cross section through an assembled implantable device of the type illustrated in FIG. 3A.

A further implementation of the present invention is illustrated in FIGS. 3A and 3B. In this implementation, any of the materials and dimensions previously discussed may be utilized and will therefore not be repeated in detail below. In this embodiment, a seed 50 comprises a rod 52 having one or more axially-extending channels 54. The channel 54 may be machined, milled, molded, stamped or otherwise created, in accordance with manufacturing techniques which will be well understood by those of skill in the art, and dependent upon the material of the rod 52.

At least one radioactive source 56 is positioned within the channel 54. An outer tubular sleeve 62 is coaxially positioned over the rod 52 both to retain the source(s) 56 within channel(s) 54 and to provide a seal between the source(s) 56 and the outside environment. One manner of accomplishing this seal is to provide the channel 54 with an axial length of less than the axial length of the rod 52. As illustrated in FIG. 3A, this permits a first sealing zone 58 at a first end of the source 56 and a second sealing zone 60 at a second end of the source 56. The sleeve 62 is configured to fit snugly around the rod 52, such that a seal is created at the sealing zones 58 and 60 to provide a seal.

Referring to FIG. 3B, one embodiment of an assembled device is illustrated in cross section. In this embodiment, four sources 56 are positioned on the rod 52, and spaced at 90° intervals. One or two or three or four or more sources 56 may be positioned circumferentially about the rod 52, depending upon the desired activity and delivered dose profile. As the number of sources 56 is increased, the radiation delivery profile of the seed 50 will approach that which would be achieved by a continuous tubular sleeve of radioactive source, concentrically positioned about the rod 52.

The present invention contemplates the use of a concentric construction in which the rod 52 carries a tubular source sleeve (not shown), which is in turn entrapped within an outer sleeve 62. In an embodiment having a cylindrical source, the source preferably resides within an annular channel on the rod 52, such that the outside diameter of the assembled source is approximately equivalent to the outside diameter of the rod 52 in the first and second seal zones 58 and 60. In this embodiment, a cylindrical source may be positioned on a rod 52 having a constant outside diameter, and held in place by positioning a short tubular locking sleeve on one or both ends of the rod in the first and second seal zones 58 and 60, as will be apparent to those of skill in the art in view of the disclosure herein. Thereafter, a constant diameter sleeve 62 may be positioned on the assembly and sealed.

Referring back to FIG. 3B, each of the channels 54 is illustrated as having a generally triangular cross section. Any of a variety of cross-sectional configurations for the channels 54 may be utilized, such as square, rectangular or radiused curve, depending upon the desired volume of the source 56 as well as the preferred manufacturing techniques for creating the channel 54.

The outer tubular sleeve 62 may be mounted on the rod 52 in any of a variety of ways, depending upon the construction materials. For example, for a metal sleeve 62 and a metal rod 52 (for example, both made of Pd—Co), the inside diameter of the sleeve 62 may be approximately equal to or slighter smaller than the outside diameter of the rod 52. The rod 52 may be cooled, and/or the sleeve 62 may be heated, to allow coaxial advancement of the sleeve 62 over the assembly of the rod 52 and the sources 56. Additional sealing steps, such as welding, may be accomplished on the axial ends of the seed 50, to ensure the integrity of the bond between the sleeve 62 and the rod 52.

Alternatively, sleeve 62 may comprise any of a variety of polymeric materials which shrink upon application of heat. A variety of heat shrink tubing materials are well understood in the catheter manufacturing arts. As a further alternative, a sleeve 62 may be applied to the rod 52 and radially outwardly facing surfaces of the sources 56 such as by dipping, spraying or wrapping operations.

In another embodiment of the current invention, a method of making an implantable seed for supplying thermal and ionizing radiation to cancerous tissue is provided. The seed comprises rod-shaped ferromagnetic alloy elements and radioactive sources.

Compositional precision is necessary to produce a ferromagnetic alloy with a specific Curie point. For example, in Pd—Co alloys, a variance in composition by as little as 0.03%, by weight, changes the Curie point by 1° C. The range of desirable Curie temperatures, 40 C. to 100 C., can be achieved by varying the composition of the Pd—Co alloy by only about 2%, i.e., from about 5.5 wt % to 7.5 wt % cobalt, as shown in Table 1 below.

TABLE 1

| Wt % Cobalt | Curie Temperature |
|---|---|
| 5.75 | 40° C. |
| 6.20 | 55° C. |
| 6.35 | 60° C. |
| 7.55 | 100° C. |

The exemplary palladium-cobalt alloy is produced preferably using an induction melting technique. Palladium and cobalt pellets or powders are placed in a sealed vessel under inert gas and melted using an induction coil. The vessel is pressurized above the vapor pressure of liquid Pd so that vaporization of this more volatile species is minimized. Preferably the vessel is designed so that the resulting Pd—Co ingot is cylindrical in shape.

The alloyed ingot cylinder, typically 6 mm to 12 mm in diameter, is then mechanically swaged and drawn into a rod of desired diameter, preferably 0.8 mm to 1.2 mm. Variations in the composition of the material can occur as the ingot is drawn out to smaller diameters. Thus, it is preferable to begin cold working the alloy only after it has been filly homogenized. High temperature annealing of the alloy slightly below the melting point, at 1000 C. to 1100 C., for a few hours appears to be sufficient to homogenize Pd—Co.

After the rods have been filly drawn and cut into appropriate lengths, they are given one final heat treatment to allow recrystallization and grain growth, as is known in the art. This annealing step can be done in a single zone furnace in an inert gas atmosphere. The rods are then furnace cooled to prevent oxidation.

The implantable seed is assembled with at least one exemplary Pd—Co alloy rod or element. Radioactive sources, preferably in the form of pellets, are positioned adjacent to the ends of the alloy element and are held in place at each end with a cylindrical tube with one closed end, which fits over the end of the element. In alternative embodiments, multiple elements are used to assemble the seed. The elements are held together by cylindrical tubes that fit over the ends of the elements, and radioactive pellets and optional spacers are positioned in the cavities in the tubes between the elements. Preferably the cylindrical tubes are made of a material that transmits radiation, such as titanium, and are sealed to the alloy elements by welding.

An external oscillating magnetic field, preferably with a maximum flux density between 25 gauss and 100 gauss and a frequency between 25 kHz and 200 kHz, is supplied, which acts upon the exemplary Pd—Co alloy elements.

Pd—Co heats up under the influence of the oscillating magnetic field until the Curie point temperature is reached.

In another embodiment, a method of treating a patient is provided. A plurality of implantable seeds, comprising ferromagnetic or other Curie point material and at least one source as discussed above, is positioned in cancerous tissue such that the longitudinal axes of the seeds are parallel. The Curie point temperature of the ferromagnetic material is in a therapeutic range. The implantable seeds are exposed to an external oscillating magnetic field aligned generally parallel to the longitudinal axes of the seeds. Under the influence of the oscillating magnetic field, the seeds heat to their Curie point temperature. Radioactive sources are positioned in cavities defined, in part, by the end caps that are attached over the ends of the implantable seeds. The radioactive sources provide ionizing radiation to treat the cancerous tissue. The radioactive sources may be, among others, palladium-103 or iodine-125.

Alternatively, each implantable seed can comprise sections of ferromagnetic material connected by hollow, tubular sleeves, in which radioactive sources and optional spacers are positioned. Preferably, the radioactive sources are positioned to produce a uniform dose profile around each implantable seed. The skilled artisan can adjust section lengths and radioactive source sizes to tailor a radiation dose profile for a particular treatment situation.

The implantable seeds can be exposed to an oscillating magnetic field for delivering heat energy to the cancerous tissue in a plurality of sessions over a course of treatment, even after the strength of the radioactive sources has diminished to sub-therapeutic levels.

In the prior art, tradeoffs have been made in an effort to maximize both ionizing radiation strength and the heating effect from the ferromagnetic material.

Solid ferromagnetic rods have been used, wherein cavities were bored into the ends for placement of radioactive pellets. This had the advantage of a solid pellet of radioactive material, which is more massive than a coating or implanted layer and is therefore a stronger radiation source. But it had the disadvantage of a relatively dense encapsulating material (e.g., Pd—Co) that was effective in attenuating ionizing radiation, and therefore reduced the amount of ionizing radiation that actually reached the surrounding tissue.

In other prior art inventions, a hollow tube of a light metal, such as titanium (Ti), has been used to encapsulate the entire implantable seed. In this case, both a ferromagnetic wire or wires and radioactive pellets were inserted into the Ti tube. This had the advantage of a strong radioactive source and good radiation transmission through the Ti tube, but had the disadvantage of a smaller heat source, since only the core of the seed contained ferromagnetic material, rather than the entire seed thickness.

The embodiments described herein have several advantages over the prior art. As discussed above, solid radioactive pellets have greater source strength than radioactive coatings or implanted layers. Also, in the current invention, a material for encapsulating the radioactive pellets can be chosen, which allows transmission of ionizing radiation from the radioactive pellet to the surrounding tissue with minimal attenuation. At the same time, heating of tumorous tissue is maximized because the ferromagnetic heating elements are made of solid material with no encapsulation. Manufacturing is relatively simple, and seeds can be economically produced.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

I claim:

1. Implantable seeds for treating soft tissue, comprising:
   rod-shaped ferromagnetic elements, each having a length and an outer diameter permitting injection and penetration thereof into the soft tissue;
   end caps configured as hollow tubes that are closed on one end and open on another end and have inner diameters sized to fit over ends of the ferromagnetic elements; and
   radioactive pellets of a size to fit inside the end caps.

2. The implantable seeds of claim 1, further comprising spacers of a size to fit inside the end caps between the ends of the ferromagnetic element and the radioactive pellets.

3. The implantable seeds of claim 2 wherein the spacers comprise a material selected from the group consisting of silica glass, silicon, beryllium and aluminum.

4. The implantable seeds of claim 1 wherein the ferromagnetic elements comprise an alloy selected from the group consisting of nickel-copper, iron -platinum, nickel-silicon, nickel palladium and palladium-cobalt.

5. The implantable seeds of claim 1 further comprising:
   hollow tubular sleeves, each having an inner diameter of a size to fit over the ends of the ferromagnetic elements, and thereby being able to connect a series of the elements; and
   radioactive pellets of a size to fit inside the hollow, tubular sleeves between the ends of adjacent ferromagnetic elements.

6. The implantable seeds of claim 5, further comprising spacers of a size to fit inside the hollow tubular sleeves between the ends of the ferromagnetic elements and the radioactive pellets.

7. The implantable seeds of claim 6 wherein the spacers comprise a material selected from the group consisting of silica glass, silicon, beryllium or aluminum.

8. The implantable seeds of claim 5 wherein the hollow tubular sleeves and the end caps both comprise titanium.

9. A therapeutic device for applying thermal and ionizing radiation to cancerous tissue, comprising:
   a rod-shaped palladium-cobalt (Pd—Co) alloy element having a length and an outer diameter permitting injection and penetration thereof into the cancerous tissue;
   a constant outer diameter of the rod-shaped element throughout a middle section of the element with step transitions to rod end sections having smaller outer diameters;
   hollow, cylindrically-shaped end caps with outer diameters the same as the outer diameter of the middle section of the rod-shaped element, inner diameters the same as the outer diameter of the rod end sections and a length at least twice as long as a length of the rod end sections, the end caps each having one closed end and one open end, the end caps fitting over the rod end sections such that the open ends of the end caps and the middle section of the rod-shaped element are adjoined together at the step transitions to form an overall smooth and continuous outer surface; and
   radioactive pellets of a size to fit into spaces remaining in the hollow end caps after the end caps have been attached to the rod end sections of the rod-shaped element.

10. The therapeutic device of claim 9, further comprising spacers that fit in the end caps between the rod end sections and the radioactive pellets.

11. The therapeutic device of claim 10 wherein the spacers comprise a material selected from the group consisting of silica glass, silicon, beryllium or aluminum.

12. The therapeutic device of claim 9 wherein the Pd—Co alloy has a predetermined Curie point temperature between about 40 C. and 100 C.

13. The therapeutic device of claim 9 wherein the Pd—Co alloy comprises a cobalt concentration between 5.5% and 7.5%, by weight.

14. The therapeutic device of claim 9 wherein the Pd—Co alloy element comprises one piece of solid material and can deliver power levels in excess of 150 mw/cm along a longitudinal dimension of the element to the cancerous tissue when the element is subjected to an oscillating magnetic field.

15. The therapeutic device of claim 14 wherein the Pd—Co alloy element comprises one piece of solid material and can deliver power levels between about 250 mw/cm and 350 mw/cm along a longitudinal dimension of the element to the cancerous tissue when the element is subjected to an oscillating magnetic field.

16. The therapeutic device of claim 9 wherein the end caps comprise titanium.

17. The therapeutic device of claim 16 wherein the end caps have walls with a thickness of between about 0.01 mm and 0.13 mm.

18. The therapeutic device of claim 9 wherein the end caps have a length of between about 2 mm and 5 mm.

19. The therapeutic device of claim 9 wherein the constant diameter of the middle section of the rod-shaped element is between about 0.8 mm and 1.2 mm.

20. The therapeutic device of claim 9 wherein the rod-shaped element has a length between about 6 mm and 14 mm.

21. The therapeutic device of claim 9 wherein the rod end sections have an outer diameter of between about 0.68 mm and 1.20 mm.

22. The therapeutic device of claim 9 wherein the length of the rod end section from the step transition to an end of the rod-shaped element is between about 0.8 mm and 1.2 mm.

23. The therapeutic device of claim 9 wherein the radioactive pellets comprise palladium-103.

24. The therapeutic device of claim 9 wherein the radioactive pellets comprise iodine-125.

25. The therapeutic device of claim 9 wherein the end caps are sealed to the rod-like element by welding.

26. An implantable seed for applying thermal and ionizing radiation to cancerous tissue, comprising:
   rod-shaped palladium-cobalt (Pd—Co) alloy elements having lengths and outer diameters permitting injection and penetration thereof into soft tissue;
   a constant outer diameter of each rod-shaped element throughout a middle section of the element with step transitions to rod end sections having smaller outer diameters;
   hollow, cylindrically-shaped, tubular sleeves, each having two open ends, each open end sized to fit over the rod end section, the tubular sleeves having the same constant outer diameter as the middle section of the rod-shaped element and having a length at least three times as long as a length of the rod end section; and
   radioactive pellets of a size that fits into a space remaining in the tubular sleeve after the tubular sleeve has made attachments at each end to the rod end sections such that the open ends of the tubular sleeves and the middle sections of the rod-shaped elements are adjoined together at the step transitions to form an implantable seed portion with smooth and continuous surfaces at the attachments.

27. The implantable seed of claim 26, further comprising spacers that fit inside the tubular sleeve between the rod end sections and the radioactive pellet.

28. The implantable seed of claim 26, further comprising hollow, cylindrically-shaped end caps, each having one closed end and one open end and fitting over outermost rod end sections of the rod-shaped elements, assembled to form an implantable seed portion, such that the open ends of the end caps and the middle sections of the rod-shaped elements are adjoined together at the step transitions to form an overall smooth and continuous outer surface.

29. The implantable seed of claim 28, further comprising radioactive pellets of a size to fit into spaces remaining in the hollow end caps after the end caps have been attached to the outermost rod end sections of the implantable seed.

30. The implantable seed of claim 29, further comprising spacers that fit in the hollow end caps between the outermost rod end sections and the radioactive pellets.

31. The implantable seed of claim 26 wherein the Pd—Co alloy has a predetermined Curie point temperature between about 40 C. and 100 C.

32. The implantable seed of claim 26 wherein the Pd—Co alloy element comprises one piece of solid material and can deliver power levels in excess of 150 mw/cm along a longitudinal dimension of the element to the cancerous tissue when the element is subjected to an oscillating magnetic field.

33. The implantable seed of claim 28 wherein the tubular sleeves and the end caps are made of a material that is a good transmitter of radiation.

34. The implantable seed of claim 33 wherein the tubular sleeves and the end caps are made of titanium.

35. The implantable seed of claim 34 wherein the tubular sleeves and the end caps have walls with a thickness of between about 0.01 mm and 0.13 mm.

36. The implantable seed of claim 26 wherein the tubular sleeves have a length of between about 3 mm and 6 mm.

37. The implantable seed of claim 26 wherein the constant diameter of the middle section of the rod-shaped element is between about 0.8 mm and 1.2 mm.

38. The implantable seed of claim 26 wherein the length of the rod-shaped element is between about 6 mm and 14 mm.

39. The implantable seed of claim 26 wherein the rod end sections have an outer diameter of between about 0.68 mm and 1.20 mm.

40. The implantable seed of claim 26 wherein the length of the rod end section from the step transition to an end of the rod-shaped element is between about 0.8 mm and 1.2 mm.

41. The implantable seed of claim 26 wherein the radioactive pellets comprise palladium-103.

42. The implantable seed of claim 26 wherein the radioactive pellets comprise iodine-125.

43. The implantable seed of claim 27 wherein the tubular sleeves and the end caps are sealed to the rod-like elements by welding.

44. An implantable seed device for treating soft tissue, comprising:
   a rod-shaped ferromagnetic element having a length and an outer diameter permitting injection and penetration thereof into soft tissue;
   at least one axially-extending channel along an outer surface of the ferromagnetic element;
   at least one radioactive source configured to fit into the at least one axially-extending channel;
   an outer tubular sleeve coaxially positioned over the rod-shaped ferromagnetic element.

45. The implantable seed device of claim 44 wherein the axially-extending channel has a length shorter than a length of the rod-shaped ferromagnetic element and is positioned on the rod-shaped ferromagnetic element to leave unchannelled sealing zones at ends of the ferromagnetic element.

46. The implantable seed device of claim 44 wherein the outer tubular sleeve is configured to fit snugly around the rod-shaped element with the at least one radioactive source in the at least one axially-extended channel and is sealed to the sealing zones.

47. The implantable seed device of claim 44 wherein a cross-sectional configuration of the axially-extending channel is selected from the group consisting of triangle, square, rectangle and radiused curve.

48. The implantable seed device of claim 44 wherein the outer tubular sleeve comprises a polymeric material.

49. The implantable seed device of claim 44 wherein the outer tubular sleeve comprises metal.

50. A method of making an implantable seed for supplying thermal and ionizing radiation to cancerous tissue, comprising:
   providing at least one rod-shaped ferromagnetic element;
   positioning radioactive sources adjacent to ends of the at least one ferromagnetic element;
   holding the radioactive sources in place at the ends of the at least one ferromagnetic element with cylindrical tubes; and
   supplying an external oscillating magnetic field to act on the at least one ferromagnetic element to produce heat therein.

51. The method of claim 50 wherein the ferromagnetic element comprises palladium-cobalt.

52. The method of claim 50 wherein the oscillating magnetic field has a maximum flux density between about 25 gauss and 100 gauss.

53. The method of claim 50 wherein the oscillating magnetic field has a frequency between about 25 kHz and 200 kHz.

54. A method of treating a patient, comprising:
   positioning a plurality of implantable seeds in cancerous tissue such that length dimensions of the implantable seeds are parallel, and the implantable seeds comprise a ferromagnetic material whose Curie point temperature is in a therapeutic range;
   providing heat from the implantable seeds by exposing the implantable seeds to an external oscillating magnetic field aligned generally parallel to the length dimensions of the implantable seeds; and
   providing ionizing radiation from radioactive sources positioned in recesses of end caps, the end caps being attached over ends of the implantable seeds.

55. The method of claim 54, further comprising providing ionizing radiation from radioactive sources positioned in recesses of hollow, tubular sleeves that connect sections of each implantable seed.

56. The method of claim 55 wherein spacing between the radioactive sources positioned in recesses of hollow, tubular sleeves is chosen to provide a uniform dose profile around each implantable seed.

57. The method of claim 54 wherein the oscillating magnetic field has a maximum flux density between about 25 gauss and 100 gauss.

58. The method of claim 54 wherein the oscillating magnetic field has a range of frequency from about 25 kHz to 200 kHz.

59. The method of claim 54 wherein the implantable seeds are exposed to the oscillating magnetic field in a plurality of sessions over a course of treatment.

60. The method of claim 54 wherein the ferromagnetic material is a binary palladium-cobalt alloy.

61. The method of claim 54 wherein the Curie point temperature is between about 40 C. and 100 C.

62. The method of claim 54 wherein the radioactive sources are selected from the group consisting of palladium-103 and iodine-125.

* * * * *